United States Patent
Fath et al.

(10) Patent No.: US 6,942,851 B2
(45) Date of Patent: Sep. 13, 2005

(54) COMPOSITION FOR THE TREATMENT OF HUMAN HAIR

(75) Inventors: Bettina Fath, Weinheim (DE); Polina Dubowoi, Bangkok (TH)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 0 days.

(21) Appl. No.: 09/975,520

(22) Filed: Oct. 11, 2001

(65) Prior Publication Data

US 2002/0110534 A1 Aug. 15, 2002

(30) Foreign Application Priority Data

Oct. 13, 2000 (DE) .......................................... 100 50 782

(51) Int. Cl.⁷ ................................................. A61K 7/06
(52) U.S. Cl. .................. 424/70.1; 424/70.9; 424/70.25; 424/600; 424/688; 424/489; 424/195.15; 424/725; 510/119
(58) Field of Search ............................... 424/70.1, 70.9, 424/600, 688, 489, 195.15, 725, 70.21; 510/119

(56) References Cited

U.S. PATENT DOCUMENTS

| | | | | |
|---|---|---|---|---|
| 5,851,544 A | * | 12/1998 | Penska et al. ............... | 424/401 |
| 6,187,298 B1 | * | 2/2001 | Kurz et al. ................... | 424/59 |
| 6,309,628 B1 | * | 10/2001 | Ansmann et al. ......... | 424/70.12 |
| 6,328,950 B1 | * | 12/2001 | Franzke et al. ............ | 424/70.6 |

FOREIGN PATENT DOCUMENTS

| | | | |
|---|---|---|---|
| DE | 1981012 | * | 5/1997 |
| EP | 0 227 994 | | 7/1987 |
| EP | 0 647 617 | | 4/1995 |
| WO | WO 92/06899 | | 4/1992 |
| WO | WO 93/10748 | | 6/1993 |
| WO | WO 94/16677 | | 8/1994 |
| WO | WO 97/15724 | | 5/1997 |

* cited by examiner

*Primary Examiner*—Thurman K. Page
*Assistant Examiner*—Lakshmi Channavajjala
(74) *Attorney, Agent, or Firm*—Norris McLaughlin & Marcus PA

(57) ABSTRACT

The invention is directed to an aqueous hair care composition comprising
a) at least one UV-absorbing substance, and
b) at least one mica/titanium dioxide pigment wherein at least 90% by weight of the mica/titanium dioxide pigment comprises a particle size between about 10 and 250 microns,
c) green tea extract, and
wherein the entire composition has a pH no greater than about 6.

18 Claims, No Drawings

COMPOSITION FOR THE TREATMENT OF HUMAN HAIR

BACKGROUND OF THE INVENTION

The present invention concerns a composition for the treatment of human hair providing it with improved properties, in particular wet and dry combability, enhanced gloss, full and yet free-flowing body as well as good hold while simultaneously exerting improved protection especially against environmental influences.

Compositions for the conditioning of human hair have been known for a long time. They generally contain quaternary ammonium compounds which bear at least one long-chain alkyl or alkenyl group, and optionally also polymers.

Such compositions are used as aqueous dispersions or emulsions, microemulsions, gels, or they are also packed as aerosols being used as hair rinses, treatments, etc. An overview of the known hair treatment products and the compositions thereof can be found in the monography of K. Schrader, "Grundlagen und Rezepturen der Kosmetika", $2^{nd}$ Ed., (1989), pages 722 to 781, in particular pages 728 to 737.

However, these known compositions can still be improved.

It has now been found that application of a hair treatment composition can provide the hair with improved properties, in particular a clearly enhanced volume effect, easier wet and dry combability as well as unobtrusive gloss, full, free-flowing texture and good hold as well as protection against negative environmental influences, if this composition on aqueous basis contains at least one mica/titanium dioxide pigment, of which at least 90% has a particle diameter in the range of about 10 to 250 microns, and at least one UV-absorbing substance.

SUMMARY OF THE INVENTION

This composition is preferably applied onto the hair after a hair wash, optionally directly subsequent to a dyeing or permanent waving treatment, preferably massaged into the hair not being removed thereafter.

The compositions are thus so-called "leave on" products, in difference to the so-called "rinse off" products, which are rinsed from the hair after a short processing period.

DETAILED DESCRIPTION OF THE PREFERRED EMBODIMENTS

Suited mica/titanium dioxide pigments are preferably present in the compostions used for the treatment of hair according to the invention in an amount from about 0.05% to about 10%, in particular bout 0.1% to about 5% by weight, in reference to the total composition. They are known per se, for example, by the name "Timiron®".

90% of the particles have a particle diameter in the range of 10 to 250 microns, 80% preferably between about 20 and 150 microns.

Suited UV-absorbing substances are preferably water-soluble UV-absorbers, however, oil-soluble UV-absorbers are basically also suited.

The UV-absorbing substance is preferably selected from at least one of the following compounds:

4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2.2'.4.4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzophenone or the sodium salt thereof, 2-hydroxy-4-octyloxybenzophenone, 2-hydroxy-4-methoxy4'-methylbenzophenone, 3-benzylidenecampher, 3-(4'-sulfo)-benzylidenebornane-2-one and the salts thereof and/or 3-(4'-methyl benzylidene)-DL-campher.

The preferred amount of the UV-absorber ranges from about 0.5% to 2.5%, preferably from 0.1% to 1% by weight, calculated to the total composition.

In addition, the compositions according to the invention contain further hair-conditioning agents.

Suited hair-conditioning polymers are customarily present in the compositions used according to the invention in an amount of about 0.25% to about 15%, in particular 0.5% to about 10%, preferably about 0.75% to 7.5% by weight, in reference to the total composition. These are, for example, cationic surfactants, especially quaternary ammonium compounds.

Suitable long-chain quaternary ammonium compounds which can be used alone or in admixture are, for example, cetyl trimethyl ammonium chloride, dimethyl dicetyl ammonium chloride, trimethyl cetyl ammonium bromide, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, behenyl trimethyl ammonium chloride, lauryl trimethyl ammonium chloride, tris-(oligooxyethyl) alkyl ammonium phosphate, cetyl pyridinium chloride, etc.

Suited are also the quaternary ammonium salts disclosed in EP-A 472 107.

Basically suitable are all quaternary ammonium compounds listed under the generic name "Quaternium" in the valid edition of the CTFA International Cosmetic Ingredient Dictionary.

Their proportion preferably ranges from about 0.5% to 10%, in particular about 1% to 7.5% by weight, calculated to the total composition.

Especially suited long-chain ammonium compounds are esterquats of the general formula (I)

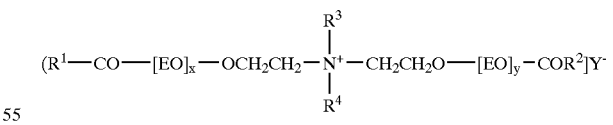

wherein $R^1$ and $R^2$ stand for an optionally hydroxy-substituted $C_8$–$C_{22}$-alkyl or alkenyl group, $R^3$ and $R^4$ stand for a $C_1$–$C_3$-alkyl group or a group —$CH_2$—$CH_2$—O-$[EO]_z$H and x, y and z stand for 0 to 5 and $Y^-$ stands for an anion.

A compound of formula I especially preferred within the scope of the invention is one wherein the groups $R^1$ and $R^2$ each stand for an oleyl group or a $C_{12}$–$C_{18}$-alkyl group, the group $R^3$ stands for a methyl group and the group $R^4$ is a group —$CH_2$—$CH_2$—O-$[EO]_z$—H.

The anion $Y^-$ is preferably a halide, such as $Cl^-$ or $Br^-$, a lower alkyl sulfate, for example, methosulfate and ethosulfate, or an alkyl phosphate, however, it is of course also possible to use other groups.

These compounds are known per se and are on the market, for example, under the trade names "Schercoquat®", "Dehyquart® F30" and "Tetranyl®".

Use of these compounds, the so-called "esterquats", in hair care compositions is known per se and described, for example, in WO-A 93/107 48, WO-A 92/068 99 and WO-A 94/166 77, wherein, however, there is no reference to the combinations according to the invention and the advantageous properties thereof.

Suited are also amidoquats of the general formula

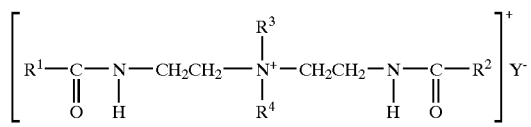

wherein $R^1$ and $R^2$ each stand for an optionally hydroxy-substituted $C_8$–$C_{22}$-alkyl or alkenyl group, $R^3$ and $R^4$ stand for a $C_1$–$C_3$-alkyl group or a group —$CH_2$—$CH_2$—O-[EO]$_x$—H, and x stands for 0 to 5, and $Y^-$ stands for an anion, Preferred groups $R^1$ and $R^2$ are $C_{12}$–$C_{18}$-alkyl- and oleyl groups, the group $R^3$ is a methyl group and the group $R^4$ is a group—$CH_2$—$CH_2$—O[EO]$_x$—H, wherein x is 0 to 3; $Y^-$ is preferably a metho sulfate, ethyl sulfate, chloride or phosphate anion.

These compounds are known per se and on the market, for example, under the trade name "INCROQUAT® HO" or "OCS".

Further suited hair-conditioning substances are synthetic or natural hair-conditioning polymers, preferably in an amount from 0.1% to 10%, in particular 0.25% to 5% by weight, calculated to the total composition.

Especially preferred are the cationic (co)polymers known by the CTFA name "Polyquaternium", however, it is also possible to nonionic, anionic and/or amphoteric polymers, for example, those of the type "Amphomer®" alone or in admixture. Additional hair-conditioning substances are lipophilic, i.e., fatty and oily substances including waxes. These are in particular natural oils, such as avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, lanolin and the derivatives thereof, as well as mineral oils such as paraffin oil and petrolatum Synthetic oils and waxes are, for example, silicone oils, polyethylenegycols, etc. Further suitable hydrophobic components are in particular fatty alcohols, especially those with about 8 to 22 carbon atoms in the molecule, such as myristyl, cetyl, stearyl alcohol, wax alcohols, and fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters such as PEG-7-glyceryl cocoate, cetyl palmitate, etc.

In the composition used according to the invention, these hydrophobic components are preferably present in a total amount ranging from about 0.5% to about 15%, in particular about 1% to 10%, especially about 1.5% to 7.5% by weight, calculated to the total composition.

An especially preferred component of the composition according to the invention is green tea extract.

This tea extract is obtained from the leaves, leaf buds and tender stems of the tea shrub, *Camellia sinensis* or *Camellia oleifera*, by aqueous or hydro-alcoholic extraction and subsequent spray-drying.

In difference to black tea, green tea is a non-fermented product obtained from the *Thea sinensis* or *Thea assamica* species.

An overview of the biological and pharmacological effects of green tea and the ingredients thereof can be found, e.g., in an article by A. Pistorius, "Seifen-Öle-Fette-Wachse-Journal", Volume 122., No. 7/1996, pages 468 to 471, to which reference is made.

The content of green tea extract is variable in the compositions according to the invention. It preferably ranges from 0.01% to 10%, preferably 0.05% to 5%, in particular 0.25% to 22.5% by weight, calculated to the total composition and the pulverulent extract.

Further suited hair-conditioning additives are ceramides of the general formula

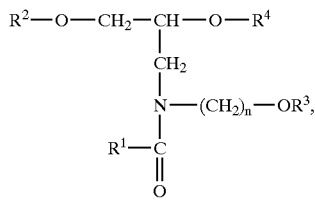

wherein $R^1$ and $R^2$ are identical or different alkyl or alkenyl groups with 10 to 22 carbon atoms, $R^3$ is hydrogen or a methyl, ethyl, n-propyl or isopropyl group, $R^4$ is hydrogen, a hydroxymethyl, hydroxyethyl, dihydroxyethyl or dihydroxypropyl group, and n is a number from 1 to 6, in particular of the type disclosed in EP 227 994 A1 and WO-A 96/37 462, however, other ceramides, for example those disclosed in WO-A 97/15724 or EP 647 617 B1, are also suited.

The preferred groups $R^1$ and $R^2$ are $C_{12}$–$C_{18}$-alkyl groups; n is a number from 1 to 3, $R^3$ is preferably hydrogen or a methyl group, and $R^4$ is hydrogen or a dihydroxypropyl group.

Especially preferred are compounds wherein $R^1$ is a $C_{12}$–$C_{24}$-alkyl group, in particular a $C_{13}H_{27}$-alkyl group, $R^2$ is a $C_{14}C_{18}$-alkyl group, in particular a $C_{16}H_{33}$-alkyl group, $R^3$ is a methyl group, $R^4$ is a

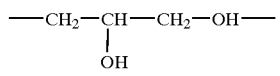

group, and n is 3, or a compound wherein $R^1$ is a $C_{15}$–$C_{31}$-alkyl group, $R^2$ stands for a $C_{16}H_{33}$-alkyl group, $R^3$ and $R^4$ each stand for a hydrogen atom and n stands for 2.

The amount thereof incorporated in the hair treatment composition used according to the invention effectively ranges from about 0.01% to 10%, preferably from about 0.05% to 7.5%, in particular from about 0.1% to 5% by weight, calculated to the total composition.

Additional suited hair-conditioning agents are water-insoluble vitamins and the derivatives thereof, for example, vitamin E and the esters thereof, such as tocopherol acetate, propionate, palmitate, etc.

Further additives, the type and quantity of which naturally depend on the application form of the composition, are fats, fatty alcohols, emulsifiers, pH-regulants, solvents and thinning agents, solubilizers, preservatives, perfumes, etc.

The compositions according to the invention can also contain surfactants.

Useful as surfactants are particularly those of the nonionic type.

Especially preferred nonionic surfactants are the known $C_8$–$C_{18}$-alkyl polyglucosides, in particular with a polycondensation degree of 1.2 to 3, especially those of the general formula $$R\!-\!O\!-\!(R^1O)_n\text{-}Z_x,$$

wherein R is an alkyl group with 8 to 18 carbon atoms, $R^1$ is an ethylene or propylene group, Z is a saccharide group with 5 to 6 carbon atoms, n is a number from 0 to 10, and x is a number between 1 and 2.5, in an amount from 1% to 10%, in particular 2.5% to 7.5% by weight, calculated to the total composition.

Other additionally useful nonionic surfactants are, for example, the various sorbitan esters, such as polyethylene glycol sorbitan stearic acid ester, fatty acid polyglycol ester or also mixed condensates of ethyleneoxide and propyleneoxide, as they are on the market, for example, under the trade name "Pluronics$^R$".

Especially suited surfactants are amphoteric and/or zwitterionic surface-active substances in an amount of about 0.5% to about 15%, preferably about 1% to about 5% by weight, calculated to the total composition.

Useful as such are in particular the various known betaines such as fatty acid amidoalkyl betaines and sulfobetaines; for example lauryl hydroxy sulfobetaine; long-chain alkyl amino acids, such as cocoaminoacetate, cocoaminopropionate and sodium cocoamphopropionate and -acetate have also proven suitable.

In detail it is possible to use betaines of the structure

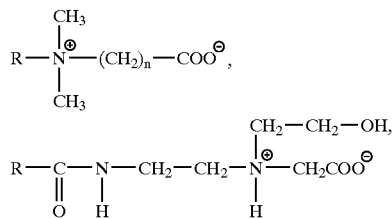

wherein R is a $C_8$–$C_{18}$-alkyl group and n is 1 to 3, sulfobetaines of the structure

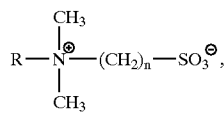

alkyl amido betaines of the general formula

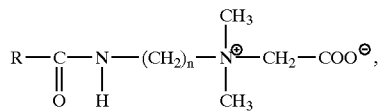

wherein R is a $C_8$–$C_{18}$-alkyl group and n is 1 to 3.

Addition of these substances especially improves the protective and conditioning properties of the product.

In addition to or in place of the named amphoteric or zwitterionic surfactants, the hair-conditioning compositions may contain at least one $C_{12}$–$C_{18}$-alkyl amidopropyl dimethyl or diethyl amine, for example, stearyl, oleyl or cocoamido propyl dimethyl amine.

The proportion thereof ranges from about 0.1% to 10%, preferably 0.25% to 5% by weight, calculated to the total composition.

A further preferred component in the compositions according to the invention are plant extracts in an amount of about 0.01% to about 10%, preferably 0.05% to 7.5%, in particular 0.1% to 5% by weight, calculated as dry residue thereof to the total composition.

Suitable aqueous (e.g. steam-distilled) alcoholic or hydroalcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol$^R$", "Sedaplant$^R$" and "Hexaplant$^R$". Extracts and the preparation thereof are also described in "Hagers Handbuch der pharmazeutischen Praxis", $4^{th}$ Ed.

The hair-treatment compositions used according to the invention are preferably present as aqueous or hydroalcoholic solution, aqueous emulsion, microemulsion, dispersion or opaque or translucent gel and can also be packed as aerosol products. Such compositions and the preparation thereof are basically known and therefore require no further explanation.

The pH-value of the compositions used according to the invention is not critical; it can preferably range between about 3 and about 8; in particular between about 4 and 6.5.

The viscosity is also in the general range and is naturally dependent on the application form of the composition.

The following Examples illustrate the invention:

EXAMPLE 1

A "leave-on" treatment of the following composition was prepared:

| | |
|---|---|
| Cetyl stearyl alcohol | 2.5 (% by wt.) |
| Isopropyl myristate | 0.2 |
| Stearamidopropyl dimethyl amine | 0.6 |
| 2-Phenyl benzimidazole-5-sulfonic acid | 0.3 |
| Lactic acid | 0.3 |
| Perfume | 0.1 |
| Green tea extract | 0.5 |
| Preservative | 0.3 |
| Mica/$TiO_2$-Pigment (Timiron ® Diamond Cluster; mean particle diameter: 90% between 20 and 150 μm) | 0.5 |
| pH-value: | ~4.5 |
| Water | ad 100.0 |

The following blind test was carried out on slightly damaged hair:

After shampooing with a customary shampoo composition, a Composition 1 according to the above Example was massaged into 5 strands of the wet hair.

Five further strands were treated in an identical manner with a Composition 1A, identical to Composition 1, however, containing no pigment particles.

Two hairdressers each evaluated the strands of hair before and after the drying according to the preference method.

| Result | Preference Composition 1 | Preference Composition 1A |
|---|---|---|
| a) Wet hair | | |
| Feeling of the hair | 4 (silky, soft, smooth) | 1 (soft, slippery) |
| Wet combability | 5 (very good) | 0 (good) |
| b) Dry hair | | |
| Volume, body | 4 | 1 |
| Hold | 4 | 1 |
| Gloss | 4 | 1 |
| Dry combability | 5 (very good) | 0 (good) |
| Texture | 5 (silky, soft, smooth from roots to ends) | 0 (harder, ends rougher) |

This result shows the surprising superiority of the composition according to the invention.

Theses differences appeared more intensively after the strands had been exposed to UV radiation for 24 hours.

EXAMPLE 2

| | |
|---|---|
| 1.2-Propyleneglycol | 2.00 (% by wt.) |
| Carbopol ®ETD 2020 (acrylates/ $C_{10}$–$C_{20}$-alkyl acrylate crosspolymer) | 0.50 |
| Cocoamidopropyl betaine | 1.00 |
| Ethanol | 17.50 |
| PPG 9 | 0.70 |
| PEG-60 hydrogenated castor oil | 0.50 |
| NaOH (32%) | 0.25 |
| Perfume | 0.10 |
| PEG-25 PABA | 0.80 |
| Almond oil | 2.00 |
| Mica/$TiO_2$-pigment (Timiron ® Diamond Cluster; 90% with mean particle diameter from 20 to 150 µm) | 0.60 |
| Water | ad 100.0 |
| pH-value: | ~6.0 |

With this product a similar improvement of the hair properties was achieved as with the product according to Example 1.

EXAMPLE 3

A styling gel of the following composition:

| | |
|---|---|
| Tocopheryl acetate | 0.5 (% by wt.) |
| Mica/$TiO_2$-pigment (Timiron ® Gleamer Flake; mean particle size: 90% between 20 and 100 µm) | 0.5 |
| Carbopol ® ETD 2001 (Carbomer) | 0.5 |
| Ethanol | 11.0 |
| Vinyl pyrrolidone/vinyl acetate copolymer (Luviskol ® VA 551) | 5.5 |
| Aminomethyl propanol | 0.4 |
| Cocoamidopropyl betaine | 1.0 |
| PEG-60 hydrogenated castor oil | 0.4 |
| Green tea extract | 0.4 |
| Perfume | 0.3 |
| Benzophenone-4 | 0.3 |
| Preservative | 0.3 |
| pH-value: | ~6.8 |
| Water | ad 100.0 | resulted in an excellent hair-conditioning effected as well as extraordinary light protection after being massaged into freshly washed hair.

EXAMPLE 4

A leave-on treatment of the composition:

| | |
|---|---|
| Cetearyl alcohol | 3.00 |
| Isopropyl palmitate | 0.20 |
| Sphingolipid E | 0.10 |
| Quaternium-80 | 0.10 |
| Mica/$TiO_2$-pigment (Timiron ® Diamond Cluster; mean particle size: 20 and 150 µm) | 0.15 |
| Green tea extract | 0.05 |
| Benzophenone-4 | 0.10 |
| Cocoamidopropyl dimethyl amine | 0.60 |
| Lactic acid | 0.35 |
| Preservative | 0.45 |
| Perfume oil | 0.20 |
| Ceteareth-20 | 0.40 |
| Water | ad 100.00 | was applied onto one half of the shampooed hair of 8 test persons according to the half-head method.

An identical composition (4A) wherein, however, the cocoamidopropyl dimethyl amine and the benzophenone-4 had been replaced by water, was massaged into the other half of the hair.

After 10 minutes processing the halves of the hair were evaluated by two experienced hairdressers, whereby neither the hairdressers nor the test persons knew which hair halves had been treated with which of the products (double-blind method).

The following result was obtained:

| Properties | Composition 4 Better | Equal | Composition 4 A Better |
|---|---|---|---|
| Wet hair | | | |
| Combability | 5 | 2 | 1 |
| Body, suppleness | 6 | 1 | 1 |
| Dry hair | | | |
| Combability | 6 | 1 | 1 |
| Body | 6 | 1 | 1 |
| Suppleness | 5 | 2 | 1 |
| Volume | 5 | 2 | 1 |
| Gloss | 5 | 2 | 1 |

What is claimed is:

1. An aqueous hair care composition for imparting improved hairstyling properties to hair, being one or more of wet combability, feeling of the hair when wet, dry combability, texture when dry and body when dry, the composition comprising,
    a) at least one UV-absorbing substance, and
    b) at least one mica/titanium dioxide pigment wherein at least 90% by weight of the mica/titanium dioxide pigment comprises a particle size between about 10 and 250 microns, and
    c) green tea extract.

2. The hair care composition according to claim 1, wherein 80% to 90% by weight of the pigment consist of mica, and 10% to 20% by weight thereof consist of titanium dioxide.

3. The hair care composition according to claim 1, containing the mica/titanium dioxide pigment in an amount between about 0.05% to about 5% by weight, calculated to the total composition.

4. The hair care composition according to claim 1, wherein the UV absorber is selected from at least one of the compounds 4-aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxy cinnamic acid and the esters and salts thereof, salicylic acid and the esters and salts thereof, 2.4-dihydroxybenzophenone, 2.2'.4.4'tetrahydroxybenzophenone, 2-hydroxy-4-methoxybenzophenone and its 5-sulfonic acid or the sodium salt thereof, 2.2'-dihydroxy-4.4'-dimethoxybenzophenone, 2-hydroxy-5chlorobenzophenone, 2.2'-dihydroxy-4-methoxybenzophenone, 2.2'-dihydroxy-4.4'dimethoxy-5.5.'-disulfobenzophenone or the sodium salt thereof, 2-hydroxy-4octyloxybenzophenone, 2-hydroxy-4-methoxy-4'methyl benzphenone, 3-benzylidene campher, 3-(4'-sulfo)-benzylidene bornane-2-one and the salts thereof and/or 3-(4'-methyl benzylidene)-DL-campher.

5. The hair care composition according to claim 1, wherein the proportion of the UV-absorber is from about 0.05% to 2.5% by weight, calculated to the total composition.

6. The hair care composition according to claim 1, wherein the wt.-% of the green tea extract is from 0.01% to 10.0% based on the total composition.

7. The hair care composition according to claim 1, wherein the composition contains about 0.1% to 5% by weight of at least one amphoteric or zwitterionic surfactant, calculated to the total composition.

8. The hair care composition according to claim 7, wherein the composition contains about 0.25% to 2.5% by weight, calculated to the total composition, of at least on betaine.

9. The hair care composition according to claim 1, wherein the composition contains about 0.1% to 10% by weight of at least one $C_{12}$–$C_{18}$-alkyl amidoprophyl dimethyl or diethyl amine.

10. The hair care composition of claim 1, wherein the composition is formulated so as to obviate the need to rinse the composition out of subject's hair.

11. A method of improving the hairstyling properties of a subject's hair with the composition of claim 1 to achieve one or more of wet combability, feeling of the hair when wet, dry combability, texture when dry and body when dry, the method comprising the steps of:
(a) treating the subject's hair, the treatment comprising of at least one treatment selected from the group consisting of washing, permanent waving, and dyeing;
(b) applying to subject's hair an amount of the composition of claim 1 that effectively imparts improved hairstyling properties to the hair being one or more of wet combability, feeling of the hair when wet, dry combability, texture when dry and body when dry.

12. The method of claim 11, wherein the composition is not rinsed from the subject's hair.

13. The method of claim 11 wherein the subject's hair is provided a permanent wave treatment immediately prior to applying the composition.

14. A leave-in hair care composition for imparting improved hairstyling properties to a subject's hair, being one or more of wet combability, feeling of the hair when wet, dry combability texture when dry and body when dry the composition comprising,
a) at least one UV-absorbing substance, and
b) at least one mica/titanium dioxide pigment wherein at least 90% by weight of the mica/titanium dioxide pigment comprises a particle size between about 10 and 250 microns, and
c) green tea extract.

15. The composition of claim 14 further comprising benzophenone.

16. The composition of claim 14 further comprising cocoamidopropyl dimethylamine.

17. The composition of claim 14 further comprising at least on $C_{12}$–$C_{18}$ alkyl amidopropyl dimethylamine.

18. The composition of claim 14 further comprising at least one $C_{12}$–$C_{18}$ alkyl amidopropyl diethylamine.

* * * * *